United States Patent [19]

Mehta et al.

[11] Patent Number: 4,975,459
[45] Date of Patent: Dec. 4, 1990

[54] MICROBICIDAL AND PLANT GROWTH REGULATING COMPOUNDS

[75] Inventors: Raj J. Mehta, King of Prussia; Colin Swithenbank, Perkasie; Zev Lidert, Doylestown; Margaret M. Bowers-Daines, Lansdale; David H. Young, Wyncote; Barry C. Lange, Lansdale, all of Pa.

[73] Assignee: Rohm and Haas Company, Philadelphia, Pa.

[21] Appl. No.: 450,127

[22] Filed: Dec. 13, 1989

[51] Int. Cl.$^5$ .................................. A01N 43/20
[52] U.S. Cl. ............................ 514/475; 71/88; 549/512; 552/223
[58] Field of Search ............ 71/88; 549/512; 552/223; 514/475

[56] References Cited

U.S. PATENT DOCUMENTS

| | | | |
|---|---|---|---|
| 2,944,870 | 7/1960 | Atkinson et al. | 552/223 |
| 2,986,569 | 5/1961 | Monroe et al. | 71/88 |
| 2,989,548 | 6/1961 | Boyd et al. | 8/39 |
| 4,400,198 | 8/1983 | Orr et al. | 71/88 |
| 4,468,245 | 8/1989 | Takematsu et al. | 71/88 |
| 4,614,521 | 9/1986 | Niwa et al. | 8/39 |
| 4,668,275 | 5/1987 | Keil et al. | 71/88 |
| 4,678,496 | 7/1987 | Motojima et al. | 71/88 |
| 4,758,262 | 7/1988 | Shapiro | 71/88 |
| 4,762,648 | 8/1988 | Stache et al. | 552/223 |
| 4,822,905 | 4/1989 | Lee et al. | 71/88 |
| 4,849,007 | 7/1989 | Rempfler et al. | 71/88 |
| 4,902,335 | 2/1990 | Kume et al. | 71/88 |

FOREIGN PATENT DOCUMENTS

| | | | |
|---|---|---|---|
| 55-136205 | 10/1980 | Japan | 71/88 |
| 59-25302 | 2/1984 | Japan | 71/88 |

OTHER PUBLICATIONS

J. Soc., Dyers Colour (181) 97 (2) 56.
Erwin, D. C. and Katznelson, K. 1971, Can J. Microbial 7, 15.
Kull, et al., Applied Microbiology, 9, 538–541 (1961).

Primary Examiner—Richard L. Raymond
Assistant Examiner—Raymond Covington
Attorney, Agent, or Firm—Michael B. Fein

[57] ABSTRACT

Process comprising the use as a microbicide or plant growth regulator of a compound of the formula

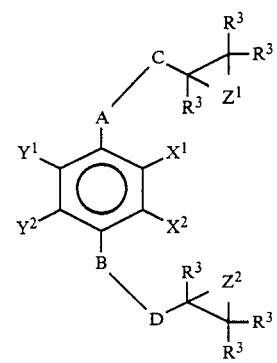

wherein
A, B, C and D is each independently selected from the group consisting of O, $NR^1$, $CR^1R^1$, CO, S, SO, and $SO_2$, except for the A-C, C-A, B-D,D-B combinations: O—O, SO—SO, $SO_2$—$SO_2$, S—O, S—$NR^2$, $SONR^2$, SO—CO, $SO_2$—CO, $SO_2$—SO;
each group of the groups $R^1$ is independently selected from the group consisting of H and $(C_1-C_4)$alkyl;
$Y^1$ and $Y^2$ may each be independently selected from the group consisting of H, $(C_1-C_4)$alkyl, halogen, OR, $SOR, SO_2R$, $SO_3R$, CN, $CO_2R$, COR, $CF_3$, $NO_2$, NHCOR, and OCOR; or alternatively $Y^1$ and $Y^2$ and the carbons to which they are attached may comprise a cyclic structure selected from the group consisting of

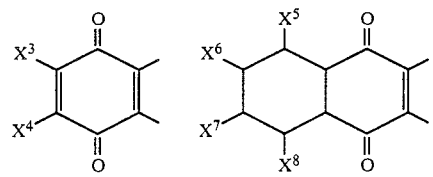

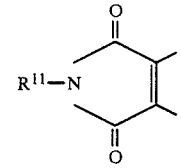

where
$R^{11}$ is aryl or $(C_1-C_4)$alkyl
$X^1$ to $X^8$ is each independently selected from the group consisting of H, $(C_1-C_4)$alkyl, halogen, OR, SOR, $SO_2R$, $SO_3R$, CN, $CO_2R$, COR, $CF_3$, $NO_2$, NHCOR, and OCOR: and furthermore optionally any pair or pairs of adjacent X's may be in the form of a divalent group attached across the adjacent X position;
$Z^1$ and $Z^2$ is each independently selected from the group consisting of $NR^2$, O, S, $CR^2R^2$ where each of the groups $R^2$ is independently selected from the group consisting of H and $(C_1-C_4)$alkyl;
each of the groups $R^3$ is independently selected from the group consisting of $CO_2R$, COR, CN $CF_3$, SOR, $SO_2R$, $(C_1-C_4)$alkyl and H.

14 Claims, No Drawings

MICROBICIDAL AND PLANT GROWTH REGULATING COMPOUNDS

BACKGROUND OF THE INVENTION

1. Field of the Invention

This invention is concerned with the use of compounds having the general structure (I) as defined hereinafter

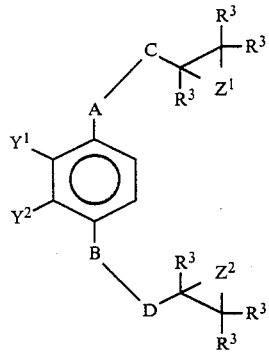

as microbicides and plant growth regulators and also with the preparation of certain novel compounds covered by this general formula. In this context, the term "microbicide" is intended to encompass but it is not restricted to bactericides, fungicides and algicides and refers to both the destruction of and the inhibition of growth of bacteria, fungi and algae. The term "plant growth regulator" means having a demonstrated and observable plant growth regulator effect, such as, for example, stunting of plant height, darkening of the hue of foliage, increase in number, size and thickness of leaves, earlier flowering and suckering.

2. Prior Art

Anthraquinones such as those having the formula

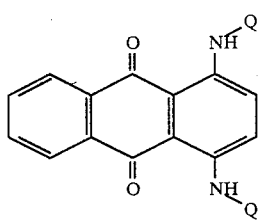

where Q=

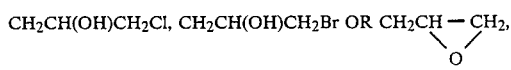

have been known for some years. The synthesis of 1,4-bis-(3-bromo-2-hydroxypropylamino)-9,10-anthracenedione is described in the U.S. Pat. No. 2,989,548 and the synthesis of 1,4-bis-(2,3-epoxypropylamino)-9,10-anthracenedione is described in J. Soc., Dyers Colour, (1981) 97 (2) 56. However the only known uses of such compounds have been in field of dyes: U.S. Pat. No. 2,944,870 describes a coloring process using a dye containing 1,4-bis-(3-chloro-2-hydroxypropylamino)-9,10-anthracenedione, and U.S. Pat. No. 4,614,521 describes a transfer recording method which uses a sublimable dye containing 1,4-bis-(2,3-epoxypropylamino)-9,10-anthracenedione. No other uses for these known anthraquinones is disclosed in the prior art.

A related known anthraquinone is 1,4-bis-(2,3-epoxypropoxy)-9,10-anthracenedione that has the formula

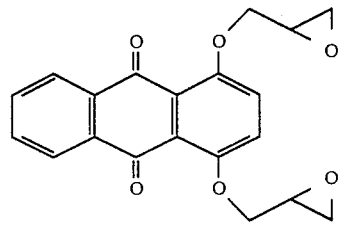

U.S. Pat. No. 4,762,648 describes the synthesis of this compound and discloses its use as an intermediate in the preparation of drugs and also as a crosslinking agent in the preparation of polymers. No other uses are disclosed.

Related naphthoquinone compounds are also known: U.S. Pat. No. 4,614,521, mentioned above, discloses as a dye a compound of the formula

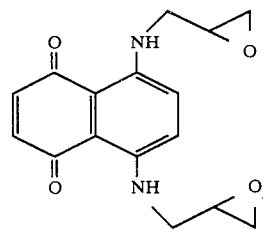

Once again, no microbicidal or plant growth regulatory use is mentioned.

SUMMARY OF THE INVENTION

We have now discovered that microbicidal and plant growth regulatory properties are possessed by compounds of the formula (I)

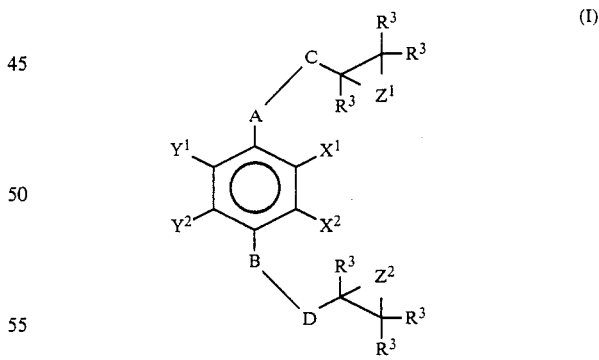

wherein
A, B, C and D is each independently selected from the group consisting of O, $NR^1$, $CR^1R^1$, CO, S, SO, and $SO_2$, except for the A-C, C-A, B-D, D-B combinations: O—O, SO—SO, $SO_2$—$SO_2$, S—O, S—$NR^2$, $SONR^2$, SO—CO, $SO_2$—CO, $SO_2$—SO;
each group of the groups $R^1$ is independently selected from the group consisting of H and $(C_1-C_4)$ alkyl;
$Y^1$ and $Y^2$ may each be independently selected from the group consisting of H, $(C_1-C_4)$alkyl, halogen, OR, SOR, $SO_2R$, $SO_3R$, CN, $CO_2R$, COR, $CF_3$, $NO_2$, NHCOR, and OCOR; or alternatively $Y^1$ and $Y^2$ and the carbons to which they are attached may comprise a cyclic structure selected from the group consisting of

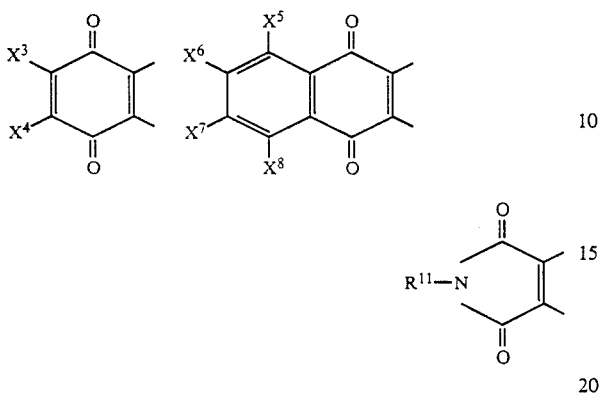

where
$R^{11}$ is aryl or $(C_1-C_4)$alkyl;
$X^1$ to $X^8$ is each independently selected from the group consisting of H, $(C_1-C_4)$alkyl, halogen, OR, SOR, $SO_2R$, $SO_3R$, CN, $CO_2R$, COR, $CF_3$, $NO_2$, NHCOR, and OCOR; and furthermore optionally any pair or pairs of adjacent X's may be in the form of a divalent group attached across the adjacent X position; $Z^1$ and $Z^2$ is each independently selected from the group consisting of $NR^2$, O, S, $CR^2R^2$ where each of the groups $R^2$ is independently selected from the group consisting of H and $(C_1-C_4)$alkyl;
each of the groups $R^3$ is independently selected from the group consisting of $CO_2R$, COR, CN, $CF_3$, SOR, $SO_2R$, $(C_1-C_4)$alkyl and H.

The divalent group or groups which are optionally present on any pairs of X positions may be trimethylene, methylene dioxyl, tetramethylene or 1,4-diketobutylene. Alternatively $X^1$, $X^2$, $X^3$, $X^4$, $X^5$, $X^6$, $X^7$ and $X^8$ may all be H.

Certain compounds of the formula (I) above may be formed in situ in an alkaline medium from compounds of the formula (II)

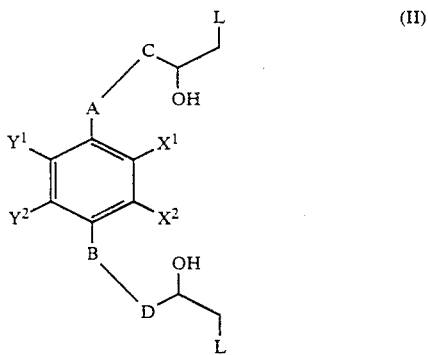

wherein A, B, $Y^1$, $Y^2$, $X^1$ and $X^2$ are as defined previously, and L is a leaving group selected from the group consiting of halogen, sulfate, substituted and unsubstituted alkyl sulfonate, and substituted and unsubstituted aryl sulfonate. The present invention also encompasses use of compounds of the formula (II) as microbicide or plant growth regulator precursors.

It has also been discovered that compositions comprising a mixture of a compound of the formula (I) as defined above and an isothiazolone have unexpected synergistic microbicidal properties. The following isothiazolone when used in conjunction with the compounds of the invention, are found to be particularly effective: 4,5-dichloro 2-n-octyl-3-isothiazolone.

In another aspect the invention provides novel compounds of the formula (III)

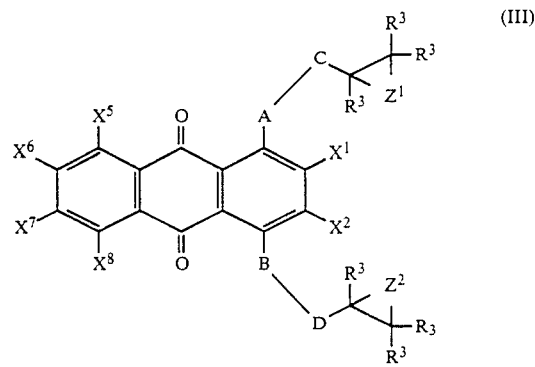

wherein A, B, C, D, E, F, $X^1$, $X^2$, $X^5$, $X^6$, $X^7$, $X^8$ are all as defined above with respect to formula (I); except wherein the microbicidal use comprises applying to a locus contaminated by or susceptible to contamination by bacteria, fungi and algae, or to a plant in the case of plant growth regulation applications, a composition containing a compound of the formula (I) in an amount sufficient to adversely affect the growth of said bacteria, fungi and algae.

The compounds of the invention can be used in any locus subject to contamination by bacteria or fungi or to regulate plant growth. Typical loci subject to contamination by bacteria are in aqueous systems such as water cooling, laundry rinse water, oil/water systems such as cutting oils, oil fields and the like where microorganisms need to be killed or where their growth needs to be controlled.

Specific loci for bacteriostatic application include disinfectants, sanitizers, cleaners, deodorizers, liquid and powder soaps, skin removers, oil and grease removers, food processing chemicals, dairy chemicals, food preservatives, animal food preservatives, wood preservatives, paint, lazures, stains, mildewcides, hospital and medical antiseptics, metal working fluids, cooling water, air washers, petroleum production, paper treatment, paper mill slimicides, petroleum products, adhesives, textiles, pigment slurries, latexes, leather and hide treatment, petroleum fuel, jet fuel, laundry sanitizers, agricultural formulations, inks, mining, nonwoven fabrics, petroleum storage, rubber, sugar processing, tobacco, swimming pools, cosmetics, toiletries, pharmaceuticals, chemical toilets, household laundry products, diesel fuel additives, waxes and polishes and other applications where water and organic materials come in contact under conditions which allow the growth of undesired microorganisms. Solutions of microbicide can also applied to a solid substrate, such as fabric, leather, or wood, as a preservative, or admixed with plastics. It is known in the art that the performance of microbicides can frequently be enhanced by combination with one or more other microbicides. In fact, there are examples of synergistic combinations of microbicides, such as those of the present invention. Thus, other known microbicides may be combined advantageously with the compounds of this invention.

See Industrial Antimicrobial Agents Encyclopedia of Chemical Technology, Volume 13, for a list of suitable other microbicides. More specific industries and applications for the compounds are:

| Industry | Application |
| --- | --- |
| Adhesives, Sealants | adhesives |
| | caulks |
| | sealants |
| Agriculture/food chain | adjuvant preservation |
| | agricultural active ingredient |
| | agricultural chemical preservative |
| | agricultural formulations preservation |
| | animal feed preservation |
| | dairy chemicals |
| | fertilizer preservation |
| | food preservation |
| | food processing chemicals |
| | grain preservation |
| | post-harvest produce protection |
| | sugar processing |
| | tobacco |
| Construction products | asphalt/concrete |
| | cement modifiers |
| | construction products |
| | roof mastics |
| | synthetic stucco |
| | wall mastics |
| | joint cement |
| Cosmetics and toiletries | cosmetics |
| | raw materials for cosmetics, toiletries |
| | toiletries |
| Disinfectants, antiseptics | antiseptic |
| | disinfectant |
| Emulsions, dispersions | aqueous dispersions |
| | dispersed pigments |
| | latex |
| | photographic emulsions |
| | pigment slurries |
| | polymer latices |
| Formulated household products | fabric softeners |
| | polishes |
| | waxes |
| | hand dish detergents |
| | raw materials |
| | liquid detergents |
| | hand soaps |
| Industrial processing, misc | electrodeposition paint, baths, rinses. |
| | electrodeposition pre-treatment, post rinses |
| | industrial fluids preservation |
| | pasteurization baths |
| | process aid preservation |
| Industrial water treatment | air washers |
| | cooling towers |
| | cooling water |
| | water cooling |
| | preservation/treatment of wooden cooling tower slats and structural members |
| | can warmers |
| | brewery pasteurization |
| | closed loop water cooling systems |
| Laundry | household laundry products |
| | laundered goods |
| | laundry wash water |
| | sanitizers-laundry |
| Leather, leather products | leather and hide |
| | leather and hide products |
| Lubricants, hydraulic aids | automotive lubricants and fluids |
| | conveyor lubricants |
| | greases |
| | hydraulic fluids |
| | lubricants |
| Medical devices | diagnostic enzymes |
| | diagnostic kits |
| | medical devices |
| Metalworking & related app's | cutting fluids |
| | metal cleaning |

-continued

| Industry | Application |
| --- | --- |
| | metalworking fluids |
| Odor control (active ingredient) | air conditioning |
| | animal bedding |
| | cat litter |
| | chemical toilet prep'ns |
| | deodorizers |
| | humidifiers |
| | industrial deodorants |
| | sanitary formulations |
| | toilet bowls |
| Paints and coatings coating | emulsions |
| | paints |
| Paper and wood pulp, their products | absorbent materials of paper and wood pulp |
| | packaging materials of paper and wood pulp |
| | paper |
| | paper products |
| | paper treatment |
| | soap wrap |
| | wood pulp |
| | wood pulp products |
| Paper mill | paper mill slimicides |
| | pulp and paper slurries |
| Petroleum refining, fuels | aviation fuels (jet fuel, aviation gas) |
| | crude oils |
| | burner, diesel and turbine fuel oils |
| | coal slurries |
| | diesel fuel additives |
| | diesel fuels |
| | fuels |
| | gasoline |
| | heating oils |
| | hydrocarbons |
| | kerosene |
| | liquefied petroleum gas |
| | petrochemical feedstocks |
| | petroleum products, storage transportation and production |
| | recycled petroleum products |
| | residual fuel oils |
| | turbine oils |
| Photographic Chemicals and process | photographic processing-wash water, rinses |
| | photoprocessing |
| | photoplate processing chemicals (developers, stabilizers etc) |
| Printing | fountain solutions (printing) |
| | ink components (pigments, resins, solvents, etc) |
| | inks |
| Sanitizers (active) | sanitizers |
| | sanitizers-dairy |
| | sanitizers-dental |
| | sanitizers-fermentation |
| | sanitizers-food preparation |
| | sanitizers-food processing |
| | sanitizers-medical |
| | sanitizers-rendering |
| | sanitizers-veterinary |
| Soaps, detergents, cleaners | cleaners |
| | detergents |
| | household cleaners |
| | industrial cleaners |
| | liquid soaps |
| | oil and grease remover |
| | powdered soaps |
| | raw materials for cleaning products |
| | soaps |
| | surfactants |
| Textiles, textile products | bonded fabrics |
| | burlap |
| | canvas |
| | canvas goods |
| | carpet backing |
| | carpets |
| | clothing |
| | coated fabrics |
| | curtains |
| | draperies |
| | engineering textiles |

| Industry | Application |
|---|---|
| | fibers |
| | geotextiles |
| | goods made of textiles |
| | knitted fabrics |
| | nets |
| | nonwoven fabrics |
| | rope |
| | rugs |
| | textile accessories |
| | textile products |
| | textiles |
| | upholstery |
| | woven fabrics |
| | yarn |
| Textile processing | dye fixatives |
| | dyes |
| | fiber lubricants |
| | hand modifiers |
| | sizes |
| | textile processing fluids |
| Therapeutic (active or preservative) | animal health/veterinary |
| | aquaculture |
| | dental |
| | human health |
| | pharmaceutical/therapeutic |
| Water purification | charcoal beds |
| | deionization resins |
| | filters |
| | membranes |
| | reverse osmosis membranes |
| | ultrafilters |
| | water purification |
| | water purification pipes, tubing |
| Wood applications | lazures (wood stains) |
| | wood |
| | wood products |
| Miscellaneous | alcohols |
| | bedding incorporating water or gels |
| | ceramic |
| | contact lens cases-leaching |
| | electronic circuitry |
| | electronics chemical |
| | enzymes-food production |
| | enzymes |
| | enzymes-industrial |
| | gel cushions |
| | marine antifoulants |
| | mildewcides |
| | wood |
| | plastics |
| | laundry |
| | mining |
| | natural rubber latex |
| | oil field injection waters including enhanced recover injection fluids, drilling, fracturing and completion fluids |
| | pipes |
| | plastics |
| | polymer systems |
| | polymers and resins (synthetic and natural) |
| | reagent preservation |
| | rubber |
| | rubber products |
| | skin remover |
| | solid protective/decorative films |
| | stains |
| | swimming pools |
| | waste treatment |
| | water beds |

When employed as agricultural fungicides, the microbicidal compounds of the invention can be applied as sprays by methods commonly employed, such as conventional high-gallonage hydraulic sprays, low-gallonage sprays, air-blast, aerial sprays and dusts. The dilution and rate of application will depend upon the type of equipment employed, the method and frequency of application desired and diseases to be controlled, but the effective amount for application is usually from about 5 grams (gm) to about 22 kilograms (kg), preferably from about 0.010 to about 1.0 kg per hectare.

The present invention is useful for the control of phytopathogenic fungi and can be utilized at various loci such as the seed, the soil or the foliage. For such purposes these compounds can be used in the technical or pure form as prepared, as solutions or as formulations. The compounds are usually taken up in a carrier or are formulated so as to render them suitable for subsequent dissemination as fungicides. For example, they can be formulated as wettable powders, emulsifiable concentrates, dusts, granular formulations, aerosols, or flowable emulsion concentrates. In such formulations, the active compounds are extended with a liquid or solid carrier and, when desired, suitable surfactants are incorporated.

It is usually desirable, particularly in the case of foliar spray formulations, to include adjuvants, such as wetting agents, spreading agents, dispersing agents, stickers, adhesives and the like in accordance with agricultural practices. Such adjuvants commonly used in the art can be found in *McCutcheon's Emulsifiers and Detergents, McCutcheon's Emulsifiers and Detergents/Functional Materials* and *McCutcheon's Functional Materials* all published annually by McCutcheon Division of MC Publishing Company (New Jersey).

An exemplary plant growth regulation application is tobacco root growth. When employed as a plant growth regulator, the compound or composition comprising the compound has a demonstrated and observable inhibitory effect on root growth. Typical effects of plant growth regulators include effects, such as, for example, stunting of plant height, darkening of the hue of foliage, increase in number, size and thickness of leaves, earlier flowering and suckering. The suckering (branching) occurs below the primary leaves and at the point of leaf stem attachments to the main stem. This branching tissue blooms and gives fruit. Plant growth regulator effects may also provide increased yields.

When used as plant growth regulators, the compounds of the invention are applied in any amount which will be sufficient to effect the desired plant response without causing any undesirable or phytotoxic response. The compounds can also be used in combination with other plant growth regulators, such as auxins, gibberellins, ethylene-releasing agents such as ethephon, pyridones, cytokinins, maleic hydrazide, succinic acid 2,2-dimethylhydrazide, choline and its salts, (2-chloromethyl) trimethylammonium chloride, triiodobenzoic acid, and the like.

DETAILED DESCRIPTION OF THE INVENTION AND THE PREFERRED EMBODIMENTS

Examples

The following examples are presented to illustrate the various aspects of the present invention. They are not to be considered as limiting.

Examples 1 to 8 demonstrate the microbicidal and antifungal activity of a preferred compound of the invention, 1,4-bis-(2,3-epoxypropylamino)-9,10-anthracenedione.

EXAMPLE 1

In vitro Fungitoxicity Assay against *Phytophthora capsici*

1,4-bis(2,3-epoxypropylamino)-9,10-anthracenedione (Test Compound) was dissolved in dimethylsulfoxide at 4 mg/ml, and 0.25 ml added to 4.75 ml of liquid asparagine-sucrose medium (Erwin, D.C. and Katznelson, K., 1971, Can. J. Microbiol; 7, 15) to give a concentration of 200 ppm. Two-fold serial dilutions of the test sample were prepared in flat-bottomed microtiter plates containing 100 μl of medium per well.

The wells were inoculated with 100 μl of *Phytophthora capsici* zoospore suspension in distilled water at $5 \times 10^4$ zoospores/ml, then incubated at 25° C. for 48 h. Minimum inhibitory concentrations ("MIC") were determined by visual inspection of fungal growth. In this case the MIC was found to be <0.1 ppm.

EXAMPLE 2

In vitro Fungitoxicity Assay against *Pythium ultimum*

A dilution series of the Test Compound was prepared in dimethylsulfoxide, and 0.1 ml of each dilution added to 19.9 ml of the aforementioned liquid asparagine-sucrose medium in 9 cm diameter perti dishes to give the desired final concentrations of test compound. Plates were inoculated with mycelial plugs, 7 mm diameter, taken from the growing edge of 48 h old cultures of *Pythium ultimum*, (ATCC 26083), grown on potato dextrose agar.

Two replicate plates were used for each treatment. The increase in mycelial dry weight was determined after growth for 48 h at 25° C. with shaking at 60 rpm. EC50 values were calculated from dose response curves; in this case the EC50 value was calculated as 0.03 ppm. Tests were also conducted on 1,4-bis(2,3-epoxypropoxy)-9,10-anthracenedione and an EC50 value of 3.6 ppm was found.

EXAMPLE 3

In vitro Toxicity Assay against Further Fungi and Bacteria

The microbicidal efficacy of the Test Compound was determined by testing a wide range of concentrations, generated by two-fold serial dilutions in a Trypticase Soy Broth (Difco) growth medium of the Test Compound against *Pseudomonas fluorescens* (ATCC# 948), *Pseudomonas aerugenosa* (ATCC# 15442), *Escherichia coli* (ATCC# 11229), *Staphylococcus aureus* (ATCC# 6538), *Aspergillus niger* (ATCC# 6275), and *Aureobasidium pullulans* (ATCC# 9348). Each test tube was inoculated to make about $1 \times 10^4$ bacteria per ml or $1 \times 10^4$ fungi per ml. The lowest concentrations of the Test Compound to inhibit visible growth (turbidity) at 37° C. for *E. coli* and at 30° C. for fungi for 7 days are the minimum inhibitory concentration (MIC). The MICs were taken as end points of antimicrobial activity.

The tests were conducted by a commonly used and accepted method described by Kull, F. C., Eisman, P. C., Sylwestrowicz, H. D. and Mayer, R. K., in Applied Microbiology 9: 538–541 (1961).

| ORGANISM | MIC (ppm) |
| --- | --- |
| P. fluorescens | <0.13 |
| P. aerugenosa | 63 |
| E. coli | 250 |
| S. aureus | <0.13 |
| A. niger | <0.13 |
| A. pullulans | <0.13 |

EXAMPLE 4

In vitro Toxicity Assay against Further Fungi

The efficacy of the Test Compound against further fungi was investigated using a modification of the test of Example 3 at a pH of 7.5. Additional fungi tested against were *Penicillium funiculosum*, *Cladosporium resinae*, *Chaetomium globosum*, and *Rhodotorula rubra*.

| ORGANISM | MIC (ppm) |
| --- | --- |
| A. niger | 0.4 |
| A. pullulans | 0.8 |
| P. fluorescens | 0.8 |
| C. resinae | 0.4 |
| C. globosum | 0.05 |
| R. rubra | >25 |

EXAMPLE 5

In vitro Toxicity Assay against Algae

The efficacy of the Test Compound against algae was determined using a culture comprising a green algae and blue green bacteria grown in an algal nutrient medium. The assay was performed by the method described in Example 3 above and incubated in the presence of fluorescent light. An MIC value of <2 ppm was determined.

EXAMPLE 6

In vivo Fungicidal Test against Cucumber Downy Mildew

*Pseudoperonospora cubensis* was maintained on leaves of live cucumber plants in a constant temperature room at about 65° to 75° F. in humid air with moderate light intensity for 7 to 8 days. A water suspension of the spores from infested leaves was obtained and the spore concentration was adjusted to about $2 \times 10^5$ spores per milliliter (ml).

Marketer cucumber seedlings were selected at their one to two true leaf stage and thinned to one plant (or two leaves) per pot. The seedlings were sprayed to runoff with a solution of the Test Compound comprising 300 ppm of the active ingredient of the Test Compound in a 2:1:1 mixture of water, acetone and methanol. After drying, a spore suspension of cucumber downy mildew was applied to the lower surface of the plant leaves with a DeVilbiss atomizer until fine droplets were visilbe on the leaves. The inoculated seedlings were placed in a humidity cabinet for 24 hours at 65° to 75° F. and then placed in a controlled temperature room. Treatment evaluations were made 7 to 8 days after inoculation. The results are reported as the percent disease control and represent the level of disease suppression when compared to the untreated control plants.

| DOSE (ppm) | PERCENT CONTROL |
| --- | --- |
| 3 | 50 |
| 12 | 90 |

| DOSE (ppm) | PERCENT CONTROL |
|---|---|
| 50 | 95 |
| 200 | 100 |

EXAMPLE 7

In vivo Fungicidal Test against Grape Downy Mildew

A water suspension of spores obtained from grape leaves infested with *Plasmopara viticola* was made up, and the spore concentration adjusted to about $4.5 \times 10^4$ spores/ml. Grape seedlings were sprayed with a solution of the Test Compound at a concentration of 200 ppm in a 2:1:1 mixture of water, acetone and methanol, and one day later the undersides of the leaves were inoculated with the spore suspension using a DeVilbiss atomizer. The inoculated seedlings were placed in a controlled temperature room for about 6 days or until chlorotic lesions were seen. Plants were evaluated by comparison with standard area diagrams. Disease severity is expressed in the results below as % disease control relative to untreated check plants.

| DOSE (ppm) | PERCENT CONTROL |
|---|---|
| 3 | 50 |
| 12 | 100 |
| 50 | 100 |
| 200 | 100 |

EXAMPLE 8

Plant Growth Regulatory Aspect of the Invention

Tobacco root assay:

A dilution series of the test compound was prepared in dimethylsulfoxide, and 20 μl of each dilution was incorporated into 20 ml of nutrient agar medium in petri dishes, 9 cm diameter. Tobacco seeds, cv. Samsung, were surface-sterilized and placed on the medium. The dishes were incubated in a vertical position at 27° C. for 7 days under a 16 h photoperiod. The length of the seedling roots was then measured. Twenty roots were measured at each treatment concentration, and EC50 values were calculated from dose response curves.

The Test Compound has an EC50 value of 0.22 ppm indicating significant plant growth regulation activity.

Comparative Examples Treflan ® and chlorpropham had values of 0.95 and 0.45, respectively.

EXAMPLE 9

In vitro Toxicity Assay against Fungi and Bacteria

The test method of example 3 was repeated with 1,4-bis -(2,3-epoxypropoxy)-9,10-anthracenedione. The results below show that significant microbicidal activity was found for the bacterium *Pseudomonas fluorescens*:

| ORGANISM | MIC (ppm) |
|---|---|
| P. fluorescens | 4 |
| P. aerugenosa | >250 |
| E. coli | >250 |
| S. aurens | >250 |
| A. niger | >250 |
| A. pullulans | >250 |

Certain microbicidal compounds of the invention may be formed in situ in a basic medium from compounds of the formula (II)

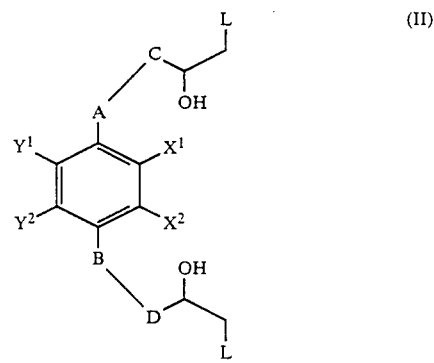

as defined previously. Tests were performed on two such compounds, and also on the epoxypropylamino compound, at varying pHs to demonstrate the improvement in microbicidal activity when such precursors are added at higher pH.

EXAMPLE 9A

In vitro Toxicity Assay against Fungi and Bacteria for 1,4-bis-(cyclopropylmethylamino) -naphthoquinone The test method of Example 3 was repeated with 1,4-bis-(cyclopropylmethylamino)-naphthoquinone. The results below show that significant microbicidal activity was found for the fungi *Aspergillus niger* and *Aureobasidium pullulans*:

| ORGANISM | MIC (ppm) |
|---|---|
| P. fluorescens | >250 |
| P. aerugenosa | >250 |
| E. coli | 250 |
| S. aureus | >250 |
| A. niger | 16 |
| A. pullulans | 63 |

EXAMPLE 9B

In vitro Toxicity Assay against Bacteria at Varying pH 1,4-bis-(2,3-epoxypropylamino)-9,10-anthracenedione, 1,4-bis-(3-chloro-2-hydroxypropylamino)-9,10 anthracenedione and 1,4-bis-(3-bromo-2-hydroxy propylamino)-9,10-anthracenedione were tested for bactericide activity against *Pseudomonas fluorescens*.

Aliquots of Mycophil ® broth were adjusted to pHs of 5.5, 7.0, 8.0 and 9.0 with either 1N HCl or 1N KOH, and then autoclaved for 15 minutes at 240° F. (115° C.). After cooling, 100 ml aliquots of the media were inoculated with 75 ml of *Pseudomonas fluorescens*, and the inoculated media transferred to micotiter test plates. The three test compounds were added at a wide range of concentrations generated by serial dilution, and the plates read after 24 hours. The lowest concentration of each test compound to inhibit visible growth at 37° C. was taken as the MIC value, as shown below.

| TEST COMPOUND | MIC (ppm) | | | |
|---|---|---|---|---|
| | pH 5.5 | pH 7.0 | pH 8.0 | pH 9.0 |
| 1,4-bis-(2,3-epoxypropylamino)-9,10-anthracenedione | 0.025 | 0.05 | 0.05 | 0.05 |
| 1,4-bis-(3-chloro-2-hydroxypro- | >100 | >100 | 50 | 50 |

-continued

| TEST COMPOUND | MIC (ppm) | | | |
|---|---|---|---|---|
| | pH 5.5 | pH 7.0 | pH 8.0 | pH 9.0 |
| pyl amino)-9,10-anthracenedione | | | | |
| 1,4-bis-(3-bromo-2-hydroxypropyl amino)-9,10-anthracenedione | 100 | 25 | 0.4 | 0.2 |

EXAMPLE 9C

In vitro Assay for Salmonellae Activity 1,4-bis(2,3-epoxypropylamino)-9,10-anthracenedione was tested against several strains of *Salmonella typhimurium* in a minimal medium containing glucose as the carbon source and ammonium chloride as the nitrogen source. Using $10^7$ test organisms, $<0.2$ ppm of 1,4-bis(2,3-epoxypropylamino)-9,10-anthracenedione completely inhibited all the strains after overnight incubation.

SYNERGISTIC COMPOSITIONS

Compounds of the invention have been found to have synergistic activity in combination with isothiazolones. The following information demonstrates this.

EXAMPLE 10

Test for Microbicidal Activity of Composition Containing 1,4-bis-(2,3-opoxypropylamino)-9,10-anthracenedione and 4,5-dichloro 2-n-octyl-3-isothiazolone The synergism of two-component compositions is demonstrated by testing a wide range of concentrations and ratios of compounds, generated by two-fold serial dilutions in a Trypticase Soy Broth (Difco) growth medium of a microbicide in one dimension and another microbicide in the second dimension, against a bacterium *Escherichia coli* (ATCC 11229), or fungi *Candida albicans* (ATCC 11651), *Aspergillus niger* (ATCC 6275), or *Aureobasidium pullulans* (ATCC 9348). Each test tube was inoculated to make about $1.5 \times 10^5$ bacteria per ml or $1.5 \times 10^5$ fungi per ml. The lowest concentrations of each compound or mixtures to inhibit visible growth (turbidity) at 37° for *E. coli* and at 30° C. for the fungi for 7 days were taken as the minimum inhibitory concentration (MIC). The MIC were taken as end points of activity. End points for the mixtures of compound A (4,5 dichloro-2-octyl-3-isothiazolone) and compound B (second component microbicide) were then compared with the end points for the isothiazolone A alone and compound B alone. Synergism was determined by a commonly used and accepted method described by Kull, F.C.; Eisman, P.C.; Sylwestrowicz, H.D. and Mayer, R.L., in applied Microbiology 9:538–541 (1961) using the ratio determined by $$Qa/QA + Qb/QB = \text{Synergy Index } (SI)$$

wherein
QA = concentration of compound A in parts per million (ppm), acting alone, which produced an end point.
Qa = concentration of compound A in ppm, in the mixture, which produced an end point.
QB = concentration of compound B in ppm, acting alone, which produced an end point.
Qb = concentration of compound B in ppm, in the mixture, which produced an end point when the sum of Qa/QA and Qb/QB is greater than one, antagonism is indicated. When the sum is equal to one additivity is indicated, and when less than one synergism is demonstrated.

In the present case, a synergy index of 0.50 was determined against *A. pullulans*.

SYNTHESIS OF COMPOUNDS

It will be appreciated by those skilled in the art that once the novel compounds of the invention are known, methods of making them may be easily devised using standard synthetic routes; although it will also be appreciated that this fact does not in any way lessen the inventiveness of the new compounds.

Preparation of the compounds which are novel and/or whose use is novel according to this inention are exemplified below.

EXAMPLE 11

Synthesis of 1,4-bis-(3-bromo-2-hydroxypropylkamino)-9,10-anthracenedione 1,4-Diaminoanthraquinone (2,5 g, 10.49 mmole) was slurried in 20 ml of glacial acetic acid. Water (1.8 ml) was added, followed by epibromohydrin (0.76 ml, 8.88 mmol). The mixture was heated to 80° C. The remaining epibromohydrin (2.24 ml, 26.18 mmol) was dripped in slowly during 5 hours, while the reaction temperature was held at 80° C. After the addition was complete, the 80° C. temperature was maintained for an additional 2 hours for a total of 7 hours. The reaction mixture was diluted with 20 ml of acetic acid and 28 ml of water. After stirring for a few minutes, the resultant mixture was filtered and the filter-cake was rinsed with 20% aqueous acetic acid followed by water, then air dried. After further drying in vacuo over $P_2O_5$, 4.76 g of 1,4-bis(3-bromo-2-hydroxypropylamino)-9,10-anthracenedione was obtained.

EXAMPLE 12

Synthesis of 1,4-bis-(3-chloro-2-hydroxypropylamino)-9,10-anthracenedione 1,4-Diaminoanthraquinone (20.00 g, 0.084 mole) was slurried in 200 ml of glacial acetic acid containing 12 ml of water. This mixture was heated to 50° C. and treated with 8.0 ml of epichlorohydrin. The reaction temperature was raised to between 90° and 100° C. and the remaining 32 ml of epichlorohydrin was dripped in slowly during 3.5 hours while maintaining this temperature range. A total of 40 ml (0.511 mole) of epichlorohydrin was added to the reaction mixture. After addition was complete, the external heating source was removed and the reaction mixture was allowed to cool to ambient temperature and stir overnight (about 16 hours). 200 ml of acetic acid containing 20% water was added to the reaction mixture and stirring was continued for 2 hours. The precipitated product was isolated by filtration. The filter-cake was rinsed with 20% aqueous acetic acid, followed by distilled water and then air-dried. This material was further dried in-vacuo over $P_2O_5$ to afford 19.08 g of 1,4-bis-(3-chloro-2-hydroxypropylamino)-9,10-anthracenedione.

EXAMPLE 13

Synthesis of 1,4-bis-(2,3-epoxypropylamino)-9,10-anthracenedione 1,4-di-(N-gamma-chloro-beta-hydroxypropylamino)-anthraquinone (15 g, 35.44 mmol) was dissolved in 225 ml of N, N-dimethylformamide containing 75 ml of ethanol. The reaction mixture was stirred vigorously, while 44.5 ml of 2N aqueous sodium hydroxide solution was added all at once. After stirring for 2 minutes, 1500 ml of water was added to the reaction mixture. Stirring was continued for 3 minutes and then the precipitated product was isolated by filtration. The filter-cake was rinsed with water and the product was dried in vacuo over $P_2O_5$ to afford a quantitative yield of 1,4-bis-(2,3-epoxypropylamino)-9,10-anthracenedione.

EXAMPLE 14

Synthesis of 1,4-bis-(cyclopropylmethylamino) naphthoquinone

According to a published procedure [*JACS* (1916)38 387], the keto-form of tetrahydroxynaphthalene was prepared from 5,8-dihydroxy-1,4-naphthoquinone as follows: 5,8-Dihydroxy-1,4-naphthoquinone (5.09 g., 26.8 mmole) was added to 1320 ml of water containing 180 ml. of concentrated hydrochloric acid and stannous chloride dihydrate (30.01 g., 133 mmole). This mixture was heated at reflux temperature for 45 minutes, then allowed to stand at room temperature for 18 hours. The reaction mixture was filtered and the isolated crystals were rinsed with water and dried in-vacuo over phosphorous pentoxide to afford 3.59 g. (69.8% yield) of the keto-form of tetrahydroxynaphthalene. $^1$H-NMR (200 MHz, CDCl$_3$)$\delta$=3.08 ppm, s, 4H; 7.28, s, 2H; 11.99, s, 2H.

Under a blanket of nitrogen (providing rigorous exclusion of air), the keto-form of tetrahydroxynaphthalene (1.00 g., 5.20 mmole) was dissolved in 3.0 ml. of absolute methanol. The methanol used as solvent was purged with nitrogen. Cyclopropylmethylamine hydrochloride (1.23 g., 11.43 mmole) and triethylamine (1.59 ml., 11.41 mmole) were dissolved in 6.0 ml. of absolute methanol and then added to the methanol solution of tetrahydroxynaphthalene. The reaction mixture was heated at 40° C. for 2 hours, then at 60° C. for 1 hour. This mixture was cooled to room temperature, treated with 3.0 ml, of N-methylpyrrolidinone and stirred, exposed to air, for 18 hr. The reaction mixture was diluted with methanol and filtered. The filter-cake was rinsed with methanol. The combined washings and filtrate were concentrated. The resultant deep blue residue was dissolved in a minimal amount of dichloromethane and chromatographed on 50 g. of silica gel, utilizing ethyl acetate/hexanes (2:1) as the eluant. The chromatography fractions containing the desired 1,4-bis-(cyclopropylmethylamino)naphthoquinone (120 mg., 8% yield) were combined and concentrated to yield a dark blue crystalline solid. m.p. 135°-138° C. $^1$H-NMR (200 MHz, CDCl$_3$) $\delta$=0.34 ppm, m,4H; 0.66,m,4H; 1.20,m,2H;3.42,t,4H;7.24, d,2H; 12.99,s,2H.

EXAMPLE 15

Synthesis of 1,4-Bis-(cyclopropylcarbonylamino) anthraquinone 1,4-Diaminoanthraquinone (2.50 g., 10.49 mmole) was slurried in 50 ml. of anhydrous toluene and cooled to 0° C. with an ice-bath. An anhydrous toluene solution (100 ml.) of cyclopropane carboxylic acid chloride (9.60 ml., 105.79 mmole) was added slowly to the anthraquinone followed by the addition of triethylamine (1.50 ml., 10.76 mmole). The ice-bath was removed and the reaction mixture stirred at room temperature for 18 hrs. The mixture was briefly heated to 90° C. (1 hour), then cooled to room temperature, diluted with toluene and filtered. The filter-cake was rinsed with toluene and the rinsings added to the filtrate. The toluene solution was washed with 3% aqueous sodium chloride solution, followed by saturated aqueous sodium chloride solution, dried with magnesium sulfate, filtered and concentrated under reduced pressure to a small volume. Hexane was added and the resultant solid precipitate was isolated by filtration to yield 310 mg. (8% yield) of 1,4-bis-(cyclopropylcarbonylamino) anthraquinone as orange-red fluffy crystals. m.p. >200° C. $^1$H-NMR (200 MHz, CDCl$_3$) $\delta$=0.8-1.25 ppm, m, 6H; 1.5-1.9,m,4H; 7.81,m,2H;8.28, m,2H; 9.14,s,2H; 12.78,s,2H.

We claim:

1. Process comprising the use as a microbicide or plant growth regulator of a compound of the formula

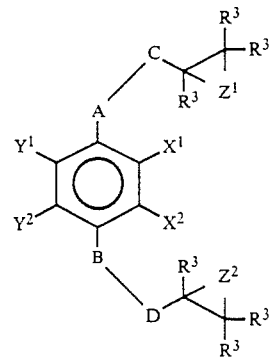

wherein

A,B,C and D is each independentl;y selected from the group consisting of O,NR$^1$, CR$^1$R$^1$, CO,S,SO, and SO$_2$, except for the A-C,C-A, B-D,D-B combinations: O—O,SO—SO,SO$_2$—SO$_2$, S—O, S-NR$^2$, SONR$^2$, SO—CO,SO$_2$—CO,SO$_2$—SO;

each group of the groups R$^1$ is independently selected from the group consisting of H and (C$_1$-C$_4$) alkyl;

Y$^1$ and Y$^2$ may each be independently selected from the group consisting of H, (C$_1$-C$_4$)alkyl, halogen, OR,-SOR, SO$_2$R,SO$_3$R,CN,CO$_2$R, COR,CF$_3$,NO$_2$, NHCOR, and OCOR; or alternatively Y$^1$ and Y$^2$ and the carbons to which they are attached may comprise a cyclic structure selected from the group consisting of

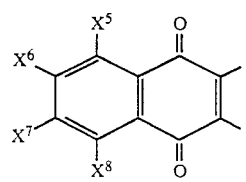

where

R$^{11}$ is aryl or (C$_1$-C$_4$)alkyl

X$^1$ to X$^8$ is each independently selected from the group consisting of H, (C$_1$-C$_4$)alkyl, halogen, OR, SOR, SO$_2$R, SO$_3$R, CN, CO$_2$R, COR, CF$_3$, NO$_2$, NHCOR, and OCOR: and furthermore optionally any pair or pairs of adjacent X's may be in the form of a divalent group attached across the adjacent X position;

$Z^1$ and $Z^2$ is each independently selected from the group consisting of $NR^2$, O, S, $CR^2R^2$ where each of the groups $R^2$ is independently selected from the group consisting of H and $(C_1-C_4)$alkyl;

each of the groups $R^3$ is independently selected from the group consisting of $CO_2R$, COR, CN $CF_3$, SOR, $SO_2R$, $(C_1-C_4)$alkyl and H wherein said compound is applied to a locus in an amount sufficient to have a microbiocidal or plant growth regulating effect.

2. Process according to claim 1 wherein $Y^1$ and $Y^2$ and the carbons to which each is attached form the structure

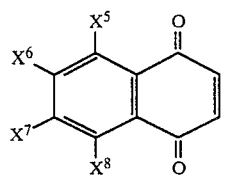

3. Process according to claim 1 wherein $Y^1$ and $Y^2$ and the carbons to which each is attached form the structure

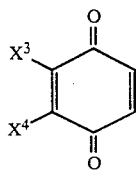

4. Process according to claim 1 wherein at least one divalent group is present across a pair of adjacent X positions and is selected from the group consisting of trimethylene, methylenedioxyl, tetramethylene, and 1,4-diketobutylene.

5. Process according to claim 1 wherein no divalent groups are attached across said adjacent positions.

6. Process according to claim 1 wherein $X^1$, $X^2$, $X^3$, $X^4$, $X^5$, $X^6$, $X^7$ and $X^8$ are all H.

7. Process according to claim 1 wherein C and D are both $CH_2$.

8. Process according to claim 1 wherein A and B are both NH.

9. Process according to claim 1 wherein $Z^1$ and $Z^2$ are both O, and all $R^3$ are H.

10. Process according to claim 1 wherein said compound is

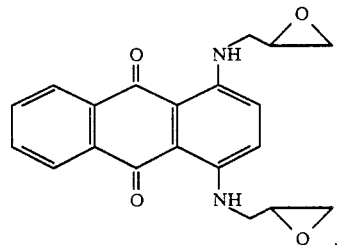

11. Process according to claim 1 wherein said compound is formed in situ in a basic medium from a compound of the formula

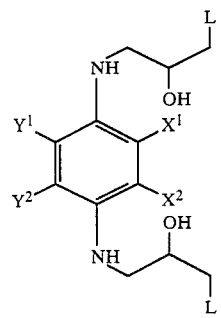

wherein L is a leaving group.

12. Process according to claim 11 wherein said leaving group is selected from the group consisting of halogen, sulfate, substituted and unsubstituted alkyl sulfonate, and substituted and unsubstituted aryl sulfonate.

13. Process according to claim 1 wherein the microbicidal use comprises applying to a locus contaminated by or susceptible to contaminative by bacteria, fungi and algae, a composition containing a compound of the formula (I) in an amount sufficient to adversely affect the growth of said bacteria, fungi and algae.

14. Process according to claim 1 wherein the microbicidal use is for control of bacteria from the genus Salmonellae.

* * * * *

UNITED STATES PATENT AND TRADEMARK OFFICE
CERTIFICATE OF CORRECTION

PATENT NO. : 4,975,459

DATED : Dec. 4, 1990

INVENTOR(S) : Raj J. Mehta et al.

It is certified that error appears in the above-identified patent and that said Letters Patent is hereby corrected as shown below: Title Page: item [75] Inventors:

Please add the following inventor after "Barry C. Lange, Lansdale, all of PA"; --Kuo-Hsuing Lee, Chapel Hill, NC--.

In the abstract, the second structure should look as follows:

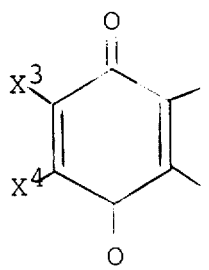 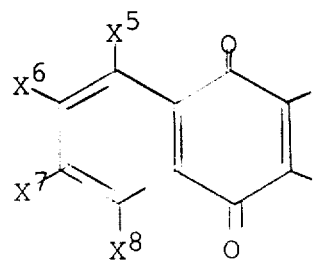 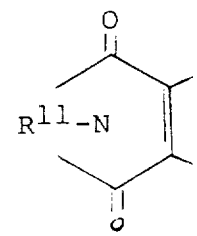

Signed and Sealed this

Fourteenth Day of July, 1992

Attest:

DOUGLAS B. COMER

Attesting Officer

Acting Commissioner of Patents and Trademarks